United States Patent
Vargas et al.

(10) Patent No.: US 6,554,764 B1
(45) Date of Patent: Apr. 29, 2003

(54) GRAFT VESSEL PREPARATION DEVICE AND METHODS FOR USING THE SAME

(75) Inventors: Jaime Vargas, Palo Alto, CA (US); Ted Bender, San Francisco, CA (US); David Bombard, San Francisco, CA (US); Jeremy Frank, Cupertino, CA (US)

(73) Assignee: Cardica, Inc., Menlo Park, CA (US)

( * ) Notice: Subject to any disclaimer, the term of this patent is extended or adjusted under 35 U.S.C. 154(b) by 249 days.

(21) Appl. No.: 09/712,044

(22) Filed: Nov. 13, 2000

(51) Int. Cl.⁷ .................................................. A61F 2/06
(52) U.S. Cl. ....................................................... 600/36
(58) Field of Search ............................... 623/1; 600/36; 606/151, 153, 205, 157, 158

(56) References Cited

U.S. PATENT DOCUMENTS

| | | |
|---|---|---|
| 3,254,650 A | 6/1966 | Collito |
| 3,519,187 A | 7/1970 | Kapitanov et al. |
| 3,774,615 A | 11/1973 | Lim et al. |
| 3,916,874 A * | 11/1975 | Perrin .................. 138/90 |
| 4,214,587 A | 7/1980 | Sakura, Jr. |
| 4,232,659 A * | 11/1980 | Dale .................. 248/201 |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,524,255 A | 6/1985 | Haag |
| 4,553,542 A | 11/1985 | Schenck et al. |
| 4,589,416 A | 5/1986 | Green |
| 4,593,693 A | 6/1986 | Schenck |
| 4,607,637 A | 8/1986 | Berggren et al. |
| 4,624,257 A | 11/1986 | Berggren et al. |
| 4,657,019 A | 4/1987 | Walsh et al. |
| 4,665,906 A | 5/1987 | Jervis |
| 4,747,407 A | 5/1988 | Liu et al. |
| 4,856,518 A * | 8/1989 | McFadden .................. 433/160 |
| 4,907,591 A | 3/1990 | Vasconcellos et al. |
| 4,917,087 A | 4/1990 | Walsh et al. |

(List continued on next page.)

FOREIGN PATENT DOCUMENTS

| | | |
|---|---|---|
| DE | 29713335.7 | 11/1997 |
| EP | 0517252 | 12/1992 |
| WO | 92/08513 | 5/1992 |
| WO | 97/25002 | 7/1997 |

(List continued on next page.)

Primary Examiner—Eric F. Winakur
Assistant Examiner—Joseph A. Cadugan
(74) Attorney, Agent, or Firm—Anthony J. Josephson; Brian A. Schar

(57) ABSTRACT

A graft vessel preparation device and a method for using the graft vessel preparation device is provided. The graft vessel preparation device establishes and maintains a critical dimension on a graft vessel which corresponds to a dimension of an anastomosis site on a target vessel. One example of a graft vessel preparation device which prepares a graft vessel for a vascular anastomosis procedure includes a parallelogram linkage, a first spreader arm and a second spreader arm. The first spreader arm and the second spreader arm mount on opposing members of the parallelogram linkage in a parallel configuration. The spreader arms are configured in order to allow the placement of an end of a graft vessel over the spreader arms. The spreader arms are also configured to separate within an interior of the graft vessel once the graft vessel is placed over the spreader arms in order to establish a critical dimension. The critical dimension is established using a critical dimension locator. The critical dimension locator allows for precise grafting of the graft vessel to a target vessel during the vascular anastomosis procedure.

64 Claims, 10 Drawing Sheets

U.S. PATENT DOCUMENTS

| | | | |
|---|---|---|---|
| 4,917,090 A | | 4/1990 | Berggren et al. |
| 4,917,091 A | | 4/1990 | Berggren et al. |
| 5,007,920 A | * | 4/1991 | Torre .................... 606/151 |
| 5,062,842 A | | 11/1991 | Tiffany |
| 5,119,983 A | | 6/1992 | Green et al. |
| 5,171,262 A | | 12/1992 | MacGregor |
| 5,217,474 A | | 6/1993 | Zacca et al. |
| 5,234,447 A | | 8/1993 | Kaster et al. |
| 5,250,060 A | | 10/1993 | Carbo et al. |
| 5,298,012 A | * | 3/1994 | Handlos .................... 269/45 |
| 5,304,220 A | | 4/1994 | Maginot |
| 5,314,468 A | | 5/1994 | Ramos Martinez |
| 5,336,233 A | | 8/1994 | Chen |
| 5,354,302 A | | 10/1994 | Ko |
| 5,366,462 A | | 11/1994 | Kaster et al. |
| 5,395,311 A | | 3/1995 | Andrews |
| 5,443,497 A | | 8/1995 | Venbrux |
| 5,456,712 A | | 10/1995 | Maginot |
| 5,456,714 A | | 10/1995 | Owen |
| 5,464,449 A | | 11/1995 | Ryan et al. |
| 5,472,404 A | * | 12/1995 | Volgushev .................... 600/36 |
| 5,478,354 A | | 12/1995 | Tovey et al. |
| 5,522,834 A | | 6/1996 | Fonger et al. |
| 5,556,405 A | | 9/1996 | Lary |
| 5,558,667 A | | 9/1996 | Yarborough et al. |
| 5,571,167 A | | 11/1996 | Maginot |
| 5,630,831 A | * | 5/1997 | Lahr .................... 606/205 |
| 5,643,340 A | | 7/1997 | Nunokawa |
| 5,669,918 A | | 9/1997 | Balazs et al. |
| 5,676,670 A | | 10/1997 | Kim |
| 5,693,088 A | | 12/1997 | Lazarus |
| 5,695,504 A | | 12/1997 | Gifford, III et al. |
| 5,702,412 A | | 12/1997 | Popov et al. |
| 5,707,362 A | | 1/1998 | Yoon |
| 5,707,380 A | | 1/1998 | Hinchliffe et al. |
| 5,709,335 A | | 1/1998 | Heck |
| 5,709,693 A | | 1/1998 | Taylor |
| 5,725,544 A | | 3/1998 | Rygaard |
| 5,725,553 A | | 3/1998 | Moenning |
| 5,732,872 A | | 3/1998 | Bolduc et al. |
| 5,797,920 A | | 8/1998 | Kim |
| 5,810,880 A | * | 9/1998 | Jensen et al. .................... 403/316 |
| 5,814,073 A | | 9/1998 | Bonutti |
| 5,817,113 A | | 10/1998 | Gifford, III et al. |
| 5,881,943 A | | 3/1999 | Heck et al. |
| 5,893,369 A | | 4/1999 | LeMole |
| 5,902,228 A | * | 5/1999 | Schulsinger et al. ........ 128/897 |
| 5,904,697 A | | 5/1999 | Gifford, III et al. |
| 5,921,995 A | | 7/1999 | Kleshinski |
| 5,944,730 A | | 8/1999 | Nobles et al. |
| 5,947,363 A | | 9/1999 | Bolduc et al. |
| 5,957,363 A | | 9/1999 | Heck |
| 5,976,159 A | | 11/1999 | Bolduc et al. |
| 6,007,544 A | | 12/1999 | Kim |
| 6,022,367 A | | 2/2000 | Sherts |
| 6,113,612 A | | 9/2000 | Swanson et al. |
| 6,132,472 A | * | 10/2000 | Bonutti .................... 600/36 |
| 6,152,937 A | | 11/2000 | Peterson et al. |
| 6,165,185 A | | 12/2000 | Shennib et al. |
| 6,368,332 B1 | * | 4/2002 | Salcudean et al. .......... 128/897 |

FOREIGN PATENT DOCUMENTS

| | | |
|---|---|---|
| WO | 97/27898 | 8/1997 |
| WO | 97/31575 | 9/1997 |
| WO | 98/07399 | 2/1998 |
| WO | 98/19618 | 5/1998 |
| WO | 98/19625 | 5/1998 |
| WO | 98/19630 | 5/1998 |
| WO | 98/19631 | 5/1998 |
| WO | 98/19632 | 5/1998 |
| WO | 98/19634 | 5/1998 |
| WO | 98/19636 | 5/1998 |
| WO | 98/196269 | 5/1998 |
| WO | 98/30153 | 7/1998 |
| WO | 98/42262 | 10/1998 |
| WO | 98/47430 | 10/1998 |
| WO | 98/55027 | 12/1998 |
| WO | 99/17665 | 4/1999 |
| WO | 99/18887 | 4/1999 |
| WO | 99/21491 | 5/1999 |
| WO | 99/38441 | 8/1999 |
| WO | 99/38454 | 8/1999 |
| WO | 99/45848 | 9/1999 |
| WO | 99/62406 | 12/1999 |
| WO | 99/62409 | 12/1999 |
| WO | 99/63910 | 12/1999 |
| WO | 99/65409 | 12/1999 |
| WO | 00/09040 | 2/2000 |

* cited by examiner

GRAFT VESSEL PREPARATION DEVICE AND METHODS FOR USING THE SAME

BACKGROUND OF THE INVENTION

1. Field of the Invention

The present invention relates generally to preparing blood vessels for a vascular anastomosis procedure and more particularly to a graft vessel preparation device which facilitates precise incision of a graft vessel for an anastomosis procedure.

2. Description of Related Art

Vascular anastomosis is a procedure where two separate blood vessels of a patient are surgically grafted together. The vascular anastomosis procedure is routinely performed during the treatment of a variety of conditions, including coronary artery disease, diseases of the great and peripheral vessels, organ transplantation and other types of trauma. When a patient suffers from coronary artery disease (CAD), an occlusion or stenosis in a coronary artery restricts blood flow to the heart muscle. In order to treat CAD, the area where the occlusion occurs is bypassed. The area is bypassed through rerouting blood flow by grafting a vessel in the form of either a prosthesis, a harvested artery or a vein. When the vessel is grafted to bypass the blocked coronary artery, the occlusion is avoided and adequate blood flow is restored to the heart muscle. This treatment is known as coronary artery bypass grafting (CABG).

When a CABG is performed, a large incision is made in the chest of a patient and the sternum is separated in order to allow access to the heart of the patient. Moreover, the patient is connected to a heart lung machine which circulates the blood of the patient. After the heart lung machine is connected to the patient, the patient's heart is stopped in order to perform the vascular anastomosis. However, stopping the patient's heart is very traumatic to the patient.

In order to minimize the trauma to the patient induced by the CABG, less invasive techniques have been used. These less invasive techniques include performing a series of small incisions in the patient's chest. Once the incisions are completed, surgery is performed with the aid of visualizing scopes. The less invasive techniques may be performed on a beating heart in order minimize trauma to the patient, thereby avoiding the need for cardiopulmonary bypass.

In both conventional and less invasive CABG techniques, a surgeon sutures one end of the graft vessel to the coronary artery and the other end of the graft vessel to a blood supplying vein or artery, such as the aorta, in order to bypass the occlusion. Prior to suturing the graft vessel to the arteries, called target vessels, an incision is made in the target vessel to allow suturing of the graft vessel to the target vessel. Typically, the surgeon cuts the incision in the target vessel to an appropriate length depending on a size of the graft vessel in order to suture the graft vessel to the target vessel. However, a great amount of skill and time is required in making the incision due to the small size of the graft vessel. Likewise, time and skill is required in aligning the graft vessel to the incision. Performing the anastomosis is further compounded by the small size and the flexible, circular configuration of the of the graft vessel. In addition, the surgeon has difficulties holding and suturing in the graft vessel due to the small size and the flexible, circular configuration of the blood vessel.

Accordingly, a need exists for an automated method which allows a surgeon to make a precise anastomosis between a graft vessel and a target vessel. This new method should implement a grafting tool which allows a surgeon to control the thin and difficult to handle tissue of the graft and target vessel. Moreover, it would be desirable to implement a grafting tool which allows for making incisions in a graft vessel to establish a predetermined length which matches a length of an incision in a target vessel.

BRIEF SUMMARY OF THE INVENTION

The present invention fills the aforementioned needs by providing a graft vessel preparation device which prepares a graft vessel for a vascular anastomosis procedure. The present invention also provides a method for preparing a graft vessel for a vascular anastomosis procedure using the graft vessel preparation device.

In one embodiment of the present invention, a graft vessel preparation device for preparing a graft vessel is disclosed. The graft vessel preparation device prepares the graft vessel for a vascular anastomosis procedure. The preparation device comprises a spreader, a critical dimension locator and a clamp. The spreader is configured to receive and stretch an end portion of the graft vessel. The critical dimension locator is configured to establish a critical dimension on the graft vessel after the graft vessel is placed over the spreader. The clamp coordinates both the spreader and the critical dimension locator in order to fix the critical dimension on the graft vessel. The critical dimension allows for precise grafting of the graft vessel to a coronary artery during a vascular anastomosis procedure.

In a further embodiment of the present invention, a graft vessel preparation device for preparing a graft vessel for a vascular anastomosis procedure is disclosed. The preparation device comprises a parallelogram linkage, a first spreader arm and a second spreader arm. The first spreader arm and the second spreader arm are mounted on opposing members of the parallelogram linkage such that the first spreader arm and the second spreader arm are parallel to one another. The parallelogram linkage also provides motion to the spreader arms whereby the spreader arms are movable with respect to each other. Also, the spreader arms are configured to receive an end of a graft vessel as the graft vessel is placed on to the graft vessel preparation device. Moreover, the spreader arms separate from one another to establish a critical dimension on the graft vessel.

In another embodiment of the present invention, a graft vessel preparation device for preparing a graft vessel for a vascular anastomosis procedure is disclosed. The graft vessel preparation device includes a base, first and second spreader arms, an extension link and a holding clamp. The base includes a first part and a second part which are movable with respect to each other. The first and second spreader arms are attached to the first and second parts of the base of the graft vessel preparation device. Also, the spreader arms are configured to receive an end of the graft vessel when the graft vessel is placed over the spreader arms. The extension link of the graft vessel preparation device is rotatably attached to the base and is configured to separate the first and second spreader arms. The holding clamp of the graft vessel preparation device is substantially aligned with the extension link and clamps the graft vessel.

In yet another embodiment of the present invention, a method for preparing a graft vessel for an anastomosis procedure using a graft vessel preparation device is disclosed. The graft vessel preparation device includes spreader arms that are movable with respect to each other. The method comprises placing the graft vessel over the spreader arms such that the spreader arms occupy an interior of the graft vessel. Once the graft vessel is placed over the spreader arms, the spreader arms are moved from one another to stretch the graft vessel. A critical dimension is then established once the graft vessel is stretched. The critical dimension is established by moving the spreader arms away from one another with the parallelogram linkage.

In a further embodiment of the present invention, a graft vessel flapper is disclosed. The graft vessel flapper comprises spreader arms which are movable with respect to each other and a clamp. The clamp, which is rotatable with respect to the spreader arms, clamps a graft vessel placed over the spreader arms. In addition, the clamp establishes a critical dimension of the graft vessel.

In another embodiment of the present invention, a method for preparing a graft vessel using a graft vessel preparation device is disclosed. The method includes forming an incision in a target vessel such that an incision perimeter is formed in the target vessel. The graft vessel is then prepared by establishing and maintaining a critical dimension of the graft vessel. The critical dimension is formed on the graft vessel such that the perimeter of the critical dimension is the same as the incision perimeter of the target vessel. The congruity of between the incision perimeter of the target vessel and the perimeter of the of the critical dimension allow for proper grafting of the graft vessel to the target vessel during a vascular anastomosis procedure.

As may be appreciated, the present invention provides a device which allows an automated method for preparing graft vessels for a vascular anastomosis procedure. The present invention precisely and accurately slices a graft vessel such that the graft vessel will graft with a coronary artery during the vascular anastomosis procedure.

BRIEF DESCRIPTION OF THE SEVERAL VIEWS OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION OF THE INVENTION

A graft vessel preparation device and a method for using the graft vessel preparation device is disclosed. As an overview, the present invention relates to a graft vessel preparation device which prepares graft vessels for a vascular anastomosis procedure. During the vascular anastomosis procedure, the graft vessel is grafted to a target vessel, such as a coronary artery. As will be discussed in much greater detail below and with respect to the accompanying Figures, the present invention allows a surgeon to make precise incisions into a graft vessel prior to grafting the vessel to an artery. Moreover, using the graft vessel preparation device, a surgeon may make the incisions to create or define a critical dimension. The critical dimension ensures proper grafting of the graft vessel to the target vessel during the vascular anastomosis procedure. Proper grafting of the graft vessel to the target vessel is ensured since an incision having the critical dimension made in the graft vessel is equivalent to an incision having the critical dimension made in the target vessel.

Figure 1:
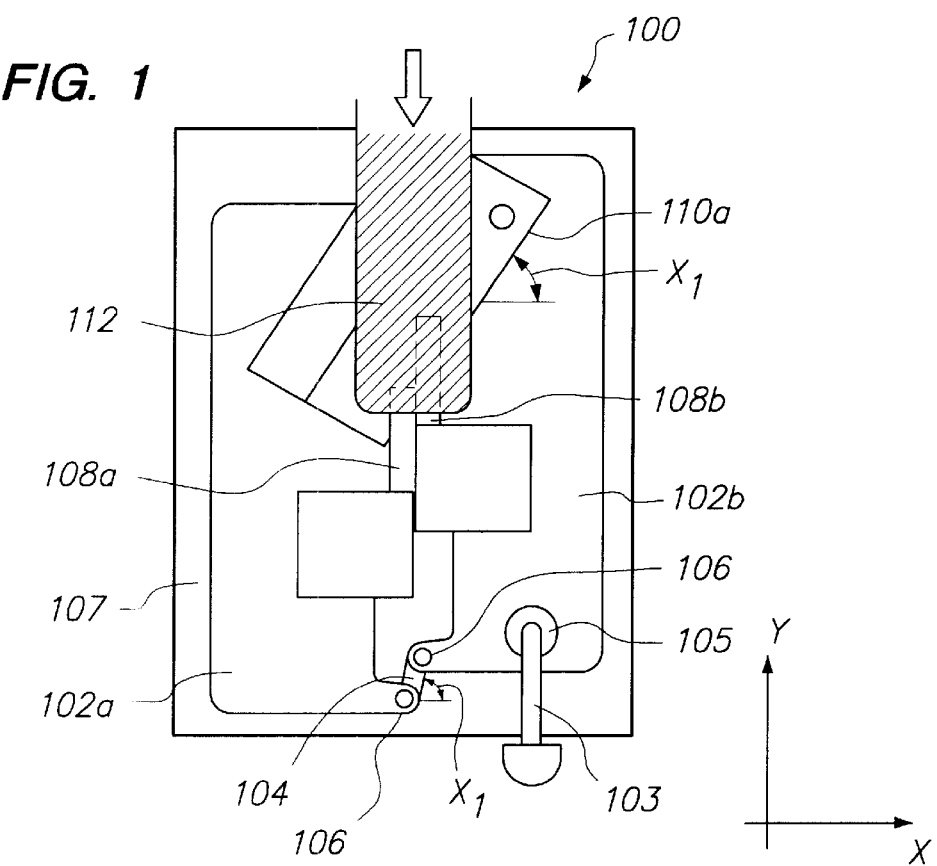
FIG. 1 is a schematic top view of a graft vessel preparation device having a graft vessel inserted over spreader arms in preparation for grafting, in accordance with one embodiment of the present invention.

Now making reference to the Figures, and more particularly to FIG. 1, FIG. 1 shows a graft vessel preparation device 100 having a graft vessel 112 inserted over spreader arms 108a and 108b in preparation for grafting. The graft vessel preparation device 100 has a first base plate 102a, a second base plate 102b, the spreader arms 108a and 108b, and an extension link 104. The graft vessel preparation device 100 also includes a first clamp portion 110a which is rotatably attached to the first base plate 102a and the second base plate 102b. The graft vessel 112 may be a vessel taken from the body of a patient, such as from the leg of the patient, a synthetic graft, or other graft to be used to bypass an occlusion during a vascular anastomosis procedure. As will be described further with respect to FIGS. 4C and 4D, the graft vessel 112 is grafted to a target vessel 124 of the patient.

The bases 102a and 102b include the spreader arms 108a and 108b, the extension link 104 and the first clamp portion 110a. The spreader arm 108a is rigidly attached to the first base plate 102a using any technique known in the art, including fasteners and machining such that the first base plate 102a and the spreader arm 108a form a single unit. The spreader arm 108b is rigidly attached to the second base plate 102b in the same manner as the spreader arm 108a is attached to the first base plate 102a. The extension link 104 rotatably attaches the first base plate 102a to the second base plate 102b with fasteners 106. The fasteners 106 may be any suitable fastener which allows rotatable connection between the extension link 104 and both the first base plate 102a and the second base plate 102b. The first clamp portion 110a is rotatably connected to both the first base plate 102a and the second base plate 102b in the same manner as the extension link 104 is attached to both the first base plate 102a and the second base plate 102b. The base plates 102a and 102b, the extension link 104 and the first clamp portion 110a together form a parallelogram linkage. In an alternative embodiment of the present invention, the base plates 102a and 102b are linkages similar to the extension link 104 such that the linkages, along with the extension link 104 and the first clamp portion 110a form a parallelogram linkage.

In one embodiment of the present invention, the base 102a is rigidly attached to a support base 107. As previously described, the extension link 104 rotatably attaches the base 102b to the base 102a. Therefore, as will be further discussed with reference to FIG. 2, as the extension link 104 rotates, the base 102b, which is not rigidly attached to the support base 107, separates from the base 102a.

Also shown with respect to FIG. 1 is the angle $X_1$. The angle $X_1$ is the angle which both the first clamp portion 110a and the extension link 104 form with respect to the X axis as shown with reference to FIG. 1. As may be seen, the first clamp portion 110a and the extension link 104 are substantially parallel with one another such that the angle $X_1$ of the extension link 104 is substantially the same as the angle $X_1$ of the first clamp portion 110a.

Furthermore, as may be seen with respect to FIG. 1, the spreaders arms 108a and 108b are adjacent to one another such that they form a single unit. The spreader arms 108a and 108b are held adjacent to each other to form the single unit with a lock. The lock may be any device suitable for holding the second base plate 102b such that the spreaders arms 108a and 108b form a single unit, such as a clamp or fasteners. In one embodiment of the present invention, a clamp 103 is used to clamp the second base plate 102b to form the single unit between the spreader arms 108a and 108b. The clamp 103 includes a grommet 105 which is in contact with the second base plate 102b when the graft vessel preparation device 100 is in a locked position. When the clamp 103 releases the second base plate 102b, the spreader arms 108a and 108b separate from one another, as shown with reference to FIG. 2.

Figure 2:
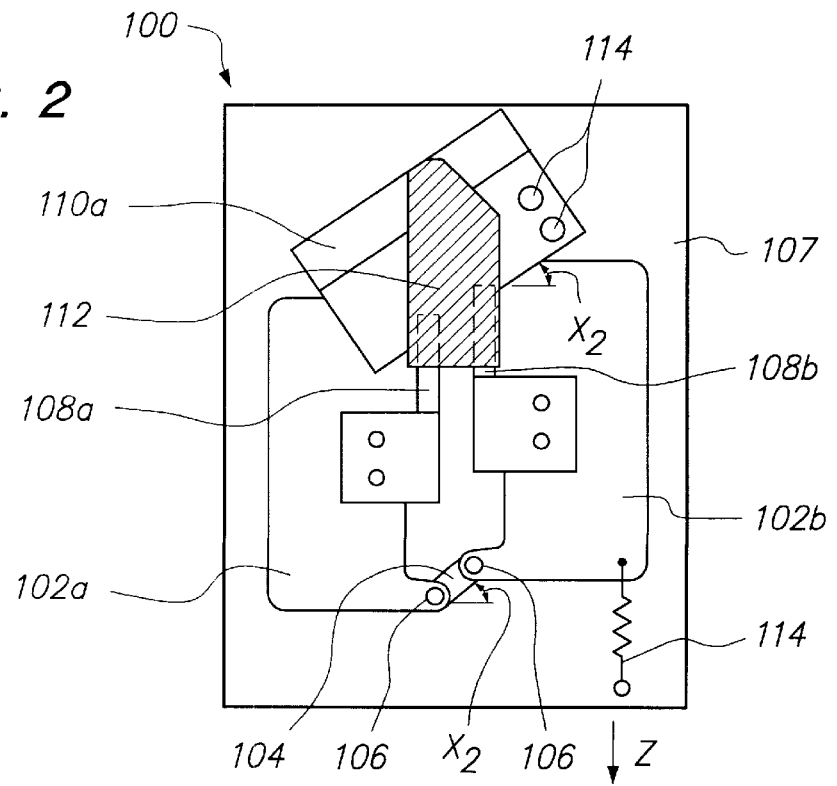
FIG. 2 illustrates a schematic top view of the graft vessel preparation device of FIG. 1 where spreader arms are separated by a tension spring, in accordance with one embodiment of the present invention.

FIG. 2 is an embodiment of the present invention where the spreader arms 108a and 108b have been separated by a tension spring 114. The tension spring 114 is rigidly attached to the second base plate 102b at one end and anchored (not shown) at the end opposite to the end rigidly attached to the second base plate 102b. The tension spring 114 is rigidly attached to the second base plate 102b with any suitable technique known in the art, such as a fastener or a clip. Once the lock is disengaged, the tension spring 114 pulls on the second base plate 102b in a downward direction, thereby separating the spreader arms 108a and 108b from each other.

A force imparted by the tension spring 114 to separate the spreader arm 108a from the spreader arm 108b may be selected such that the spreader arms exert a force within the graft vessel 112 in a range preferably between about 40 mm Hg and about 100 mm Hg, and more preferably about 60 mm Hg. This allows the graft vessel 112 to be stretched by the graft preparation device to a condition which accurately mimics the condition of the graft vessel after completion of the anastomosis. In this embodiment, the tension spring 114 has a pretension of about 0.2 lbs., a rate between about 0.1 lb./in. to about 1 lb./in. and a length of about 1 inch.

As the tensile spring 114 pulls on the second base plate 102b to separate the spreader arms 108a and 108b from each other, the extension link 104 rotates to an angle $X_2$ with respect to the X axis to separate the first base plate 102a from the second base plate 102b. When the extension link 104 rotates, the spreader arms 108a and 108b separate from one another since the spreader arms 108a and 108b are rigidly attached to the base plates 102a and 102b. The tensile spring 114 continues to separate the spreader arms 108a and 108b from one another until the movement of the spreader arms 108a and 108b is limited by the fully extended the graft vessel 112. After the spreader arms 108a and 108b come into contact with the interior walls of the graft vessel 112 and stretch the graft vessel 112 to the desired amount, a second clamp portion 110b is attached to the first clamp portion 110a, as shown with respect to FIG. 3.

Figure 3:
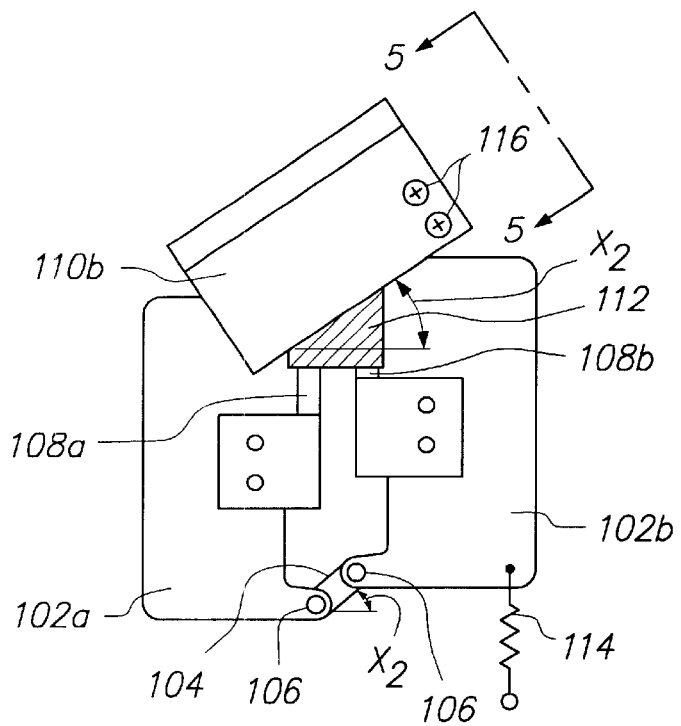
FIG. 3 is a top view of the graft vessel preparation device of FIG. 2 which shows a second clamp portion attached to a first clamp portion, in accordance with one embodiment of the present invention.

FIG. 3 shows the second clamp portion 110b attached to the first clamp portion 110a to trap the graft vessel 112 in a clamp 110, in accordance with one embodiment of the present invention. The second clamp portion 110b attaches to the first clamp portion 110a using fasteners 116. The fasteners 116 may be any suitable type of fastener which securely fastens the second clamp portion 110b to the first clamp portion 110a, such as a threaded fastener or the like. In an alternative embodiment of the present invention, the clamp 110 may have a single-piece hinged design where the clamp 110a is rotatably attached with the clamp 110b with any suitable technique, such as a hinge or the like. When the second clamp portion 110b is attached to the first clamp portion 110a, the angle $X_2$ is maintained such that the second clamp portion 110b is substantially aligned with the extension link 104. Once the second clamp portion 110b is attached to the first clamp portion 110a, the graft vessel 112 is trapped by the clamp 110. When the graft vessel 112 is trapped by the clamp 110, the graft vessel 112 is ready for incision, or in an alternative embodiment, eversion. It should be noted that the trapped graft vessel 112 is sufficiently flattened by the clamp 110 to hold the graft vessel 112 in place without damaging the graft vessel 112.

Figure 4A:
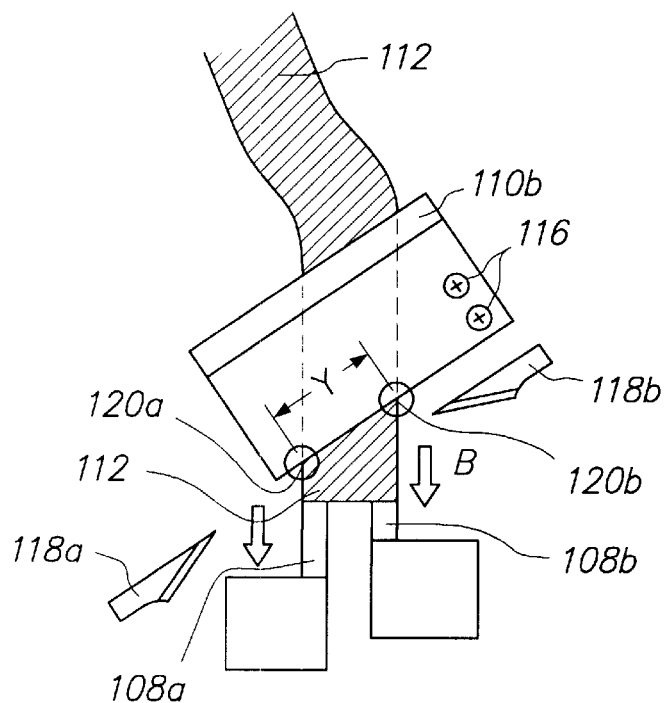
FIG. 4A is a schematic top view of the graft vessel preparation device of FIG. 3 illustrating incisors slicing a graft vessel, in accordance with one embodiment of the present invention.

Now making reference to FIG. 4A, FIG. 4A illustrates incisors 118a and 118b slicing the graft vessel 112, in accordance with one embodiment of the present invention. The incisors 118a and 118b may be any type of device suitable for slicing a graft vessel, such as a scalpel, a knife, scissors, shears, or the like. The incisors 118a and 118b begin slicing the graft vessel 112 at incision points 120a and 120b. The incision points 120a and 120b define a critical dimension Y, as shown more clearly with reference to FIG. 4B.

Figure 4B:
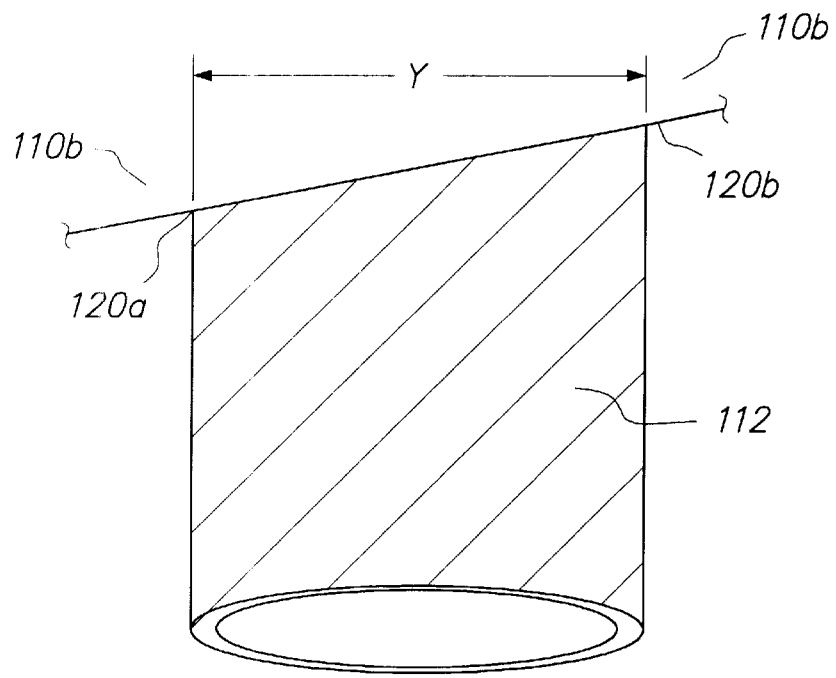
FIG. 4B shows perspective view of a graft vessel more clearly illustrating a critical dimension Y on the graft vessel, in accordance with one embodiment of the present invention.

FIG. 4B shows the critical dimension Y on the graft vessel 112, in accordance with one embodiment of the present invention. The critical dimension Y is defined by the incision points 120a and 120b along the graft vessel 112. The incision points 112a and 112b are defined as the points where the first clamp portion 110a and the second clamp portion 110b intersect with the graft vessel 112. The defining and maintaining of critical dimension Y with the clamp 110 allows for proper grafting of the graft vessel to a target vessel during the vascular anastomosis procedure. To further illustrate the anastomosis procedure, reference is now made to FIG. 4C.

Figure 4C:
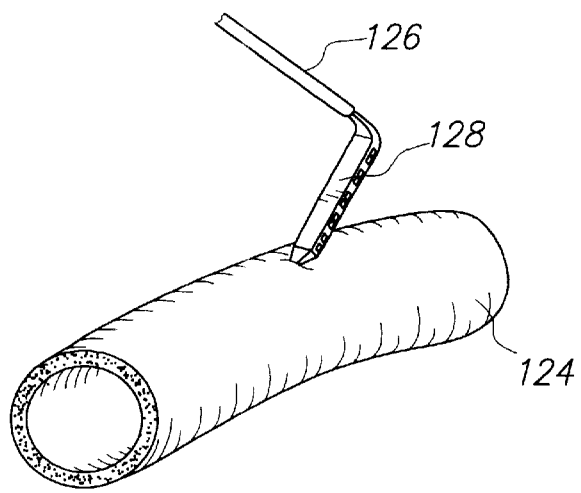
FIG. 4C illustrates an isometric view of the insertion of a anastomosis tool having an anvil into a target vessel, in accordance with one embodiment of the present invention.

FIG. 4C illustrates the insertion of a anastomosis tool 126 having an anvil 128 into a target vessel 124. In order to graft the graft vessel 112 to the target vessel 124 during the vascular anastomosis procedure, an incision must be made in the target vessel 124 which allows the grafting of the graft vessel 112 to the target vessel 124. In order to make the incision, the anvil 128 of the anastomosis tool is first inserted into the target vessel 124. After the anvil 128 is inserted into the target vessel 124 the anvil is lifted in order to stabilize a wall of the target vessel 124 at the anastomosis site, as shown with reference to FIG. 4D.

Figure 4D:
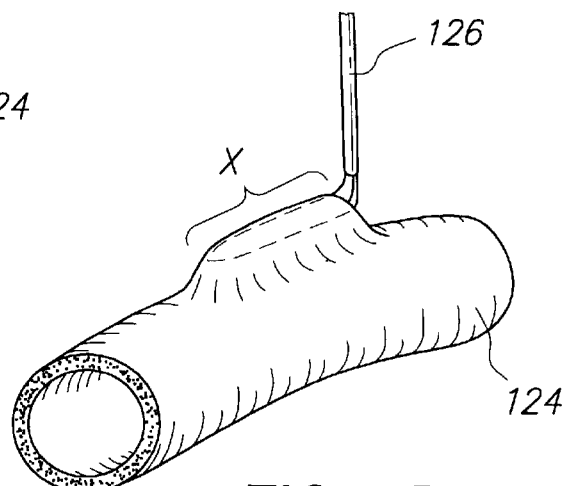
FIG. 4D is an isometric view of the target vessel showing the stabilization of target vessel after the anvil is inserted into the target vessel.

FIG. 4D illustrates the stabilization of the target vessel 124 after the anvil 128 is inserted into the target vessel 124. Once the anvil 128 is lifted to stabilize the target vessel 124, a critical dimension X is established along the target vessel 124 as shown with reference to FIG. 4D. The critical dimension X corresponds substantially to the length of the anvil 128 along which the graft vessel 112 will be stapled, sutured or otherwise connected. In accordance with one embodiment of the present invention, the critical dimension Y established by the incision points 120a and 120b is equal or substantially equal to the critical dimension X formed by the anvil 128. A length on an incision made in the target vessel 124 is substantially the same as the critical dimension X. The incision may be made before or after the graft vessel 112 is connected to the target vessel 124. Therefore, the formation of the critical dimension Y along the graft vessel 112 ensures that the graft vessel 112 will be properly grafted to the target vessel 124 during the grafting procedure.

Turning back to FIG. 4A, once the incisors 118a and 118b are placed at the incision points 120a and 120b, the graft vessel 112 is sliced by the incisors 118a and 118b in a direction depicted by directional arrows B. As the incisors 118a and 118b slice the graft vessel 112, the incisors 118a and 118b may be guided by grooves 101 in the spreader arms 108a and 108b, as shown with reference to FIG. 4E. It should be noted that the critical dimension Y may also be maintained using other suitable techniques in addition to slicing the graft vessel, such as everting the graft vessel, or the like. In addition, in an alternative embodiment of the present invention, the spreader arms 108a and 108b may be removed from the graft vessel 112 and the graft vessel 112 may be sliced with scissors or a similar apparatus. In this alternative embodiment, the clamp 110 maintains the critical dimension of the graft vessel 112 as the graft vessel 112 is sliced with scissors starting at the incision points 120a and 120b.

Figure 4E:
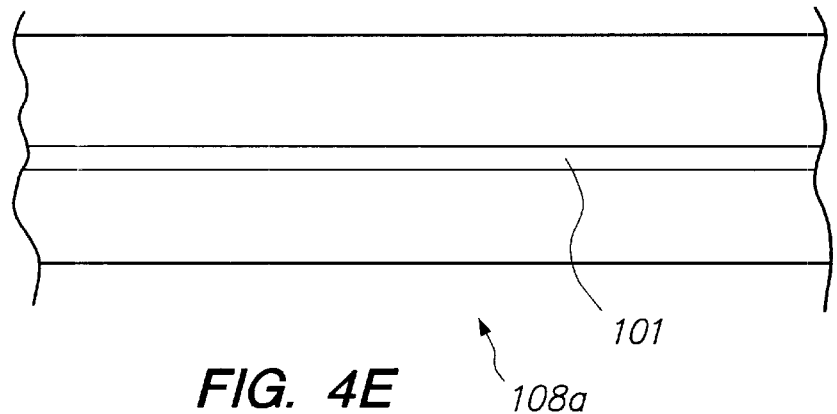
FIG. 4E shows a side view of the spreader arm of FIG. 4A which more clearly shows grooves in the side of the spreader arm, in accordance with one embodiment of the present invention.

Now making reference to FIG. 4E, FIG. 4E shows the groove 101 in one of the spreader arms 108a or 108b, in accordance with one embodiment of the present invention. The groove 101 guides the incisor 118a as the incisor 118a slices the graft vessel 112. The groove 101 also provides a hard surface for the incisor 118a as the incisor 118a slices the graft vessel 112. It should be noted that the spreader arm 108b also includes a groove (not shown) which guides the incisor 118b as the incisor 118b slices the graft vessel 112.

Figure 5:
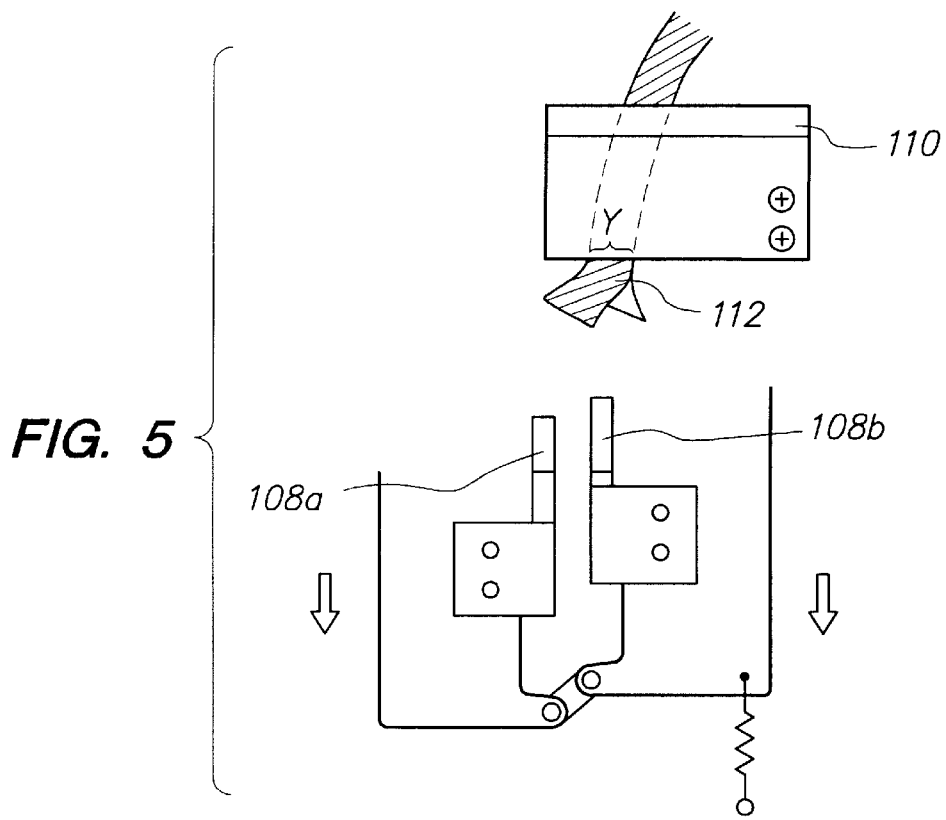
FIG. 5 illustrates a schematic top view of the graft vessel preparation device of FIG. 4A where the graft vessel is removed from the graft vessel preparation device, in accordance with one embodiment of the present invention.

Now making reference to FIG. 5, FIG. 5 illustrates removing the graft vessel 112 from the graft vessel preparation device 100, in accordance with one embodiment of the present invention. Once the incisions are made in the graft vessel 112 with the incisors 118a and 118b, the graft vessel 112 is removed from the graft vessel preparation device 100. The clamp 110, which is formed by the first clamp portion 110a and the second clamp portion 110b, is used to hold the graft vessel 112 during removal of the graft vessel 112 from the graft vessel preparation device 100. The clamp 110 maintains the critical dimension Y of the graft vessel as the clamp 110 is attached to an automated anastomosis tool 132, as will be described in greater detail with respect to FIG. 7. It should be noted that any device capable of holding the graft vessel 112 may be substituted for the clamp 110. The clamp 110 is configured to attach to the anastomosis tool 132, as shown with reference to FIG. 6.

Figure 6:
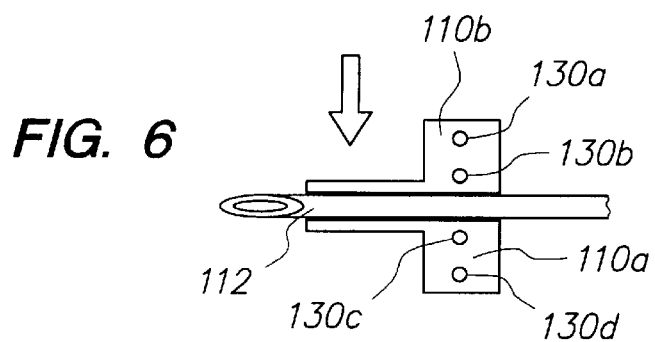
FIG. 6 is a side view of the clamp of the graft vessel preparation device of FIG. 5 formed by a first clamp portion and a second clamp portion in accordance with one embodiment of the present invention.

FIG. 6 is a side view of the clamp 110 which is formed by the first clamp portion 110a and the second clamp portion 110b, in accordance with one embodiment of the present invention. The first clamp portion 110a and the second clamp portion 110b contain alignment holes 130a through 130d. The alignment holes 130a through 130d align the clamp 110 with the anastomosis tool 132. It should be noted that other alignment features may be used to align the clamp 110 with the anastomosis tool 132, such as a dovetail groove or the like. Also, the alignment holes 130a through 130d facilitate proper engagement of the clamp 110 with the anastomosis tool 132, as shown with reference to FIG. 7.

Figure 7:
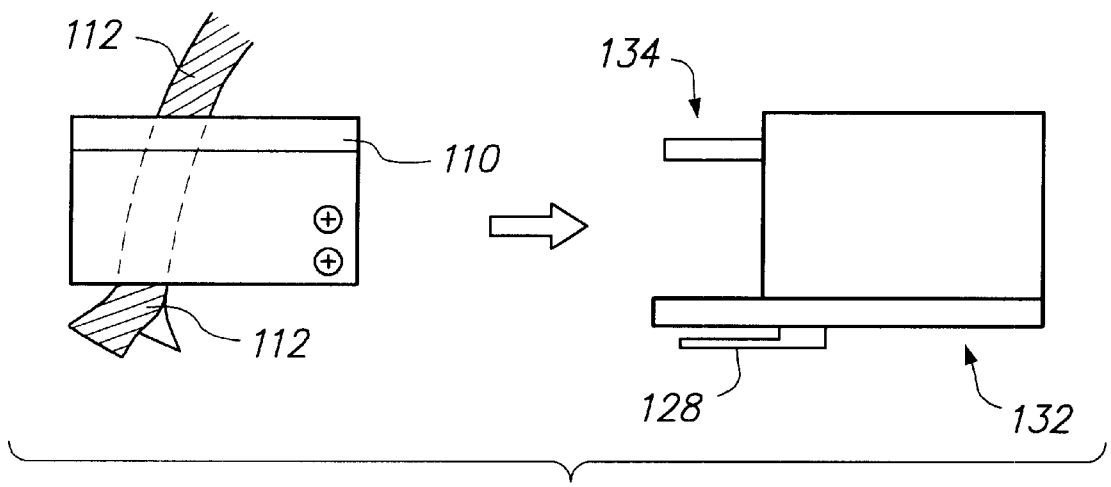
FIG. 7 illustrates a side view of the clamp of FIG. 6 being inserted onto a anastomosis tool in accordance with one embodiment of the present invention.

FIG. 7 illustrates the insertion of the clamp 110 onto the anastomosis tool 132 in accordance with one embodiment of the present invention. The anastomosis tool 132 performs an anastomosis by connecting the graft vessel 112 to the target vessel 124. One example of an anastomosis tool which may be used is described in U.S. patent application Ser. No. 09/363,255, which is incorporated herein by reference in its entirety. The clamp 110 and the graft vessel 112 must be attached to the anastomosis tool in order to complete the vascular anastomosis procedure. After the graft vessel 112 is sliced and removed from the graft vessel preparation device 100 using the clamp 110, the clamp 110 is transferred to the anastomosis tool 132 and attached to the anastomosis tool 132 via the alignment holes 130a through 130d. The alignment holes 130a through 130d fit over corresponding alignment pins 134 of the anastomosis tool 132. The alignment pins 134 ensure that the graft vessel 112 fits properly within the anastomosis tool 132 in order to allow proper grafting of the graft vessel 112 with the target vessel 124. The alignment pins 134 are rigidly attached to the anastomosis tool 132 by any suitable means, including pressing or molding the alignment pins 134 with the anastomosis tool 132 from a single material, such as acrylonitrite butadiene styrene (ABS) or polycarbonate; or threaded fasteners or the like. Once the clamp 110 along with the graft vessel 112 is attached to the anastomosis tool 132, the vascular anastomosis procedure may be performed.

Figure 8:
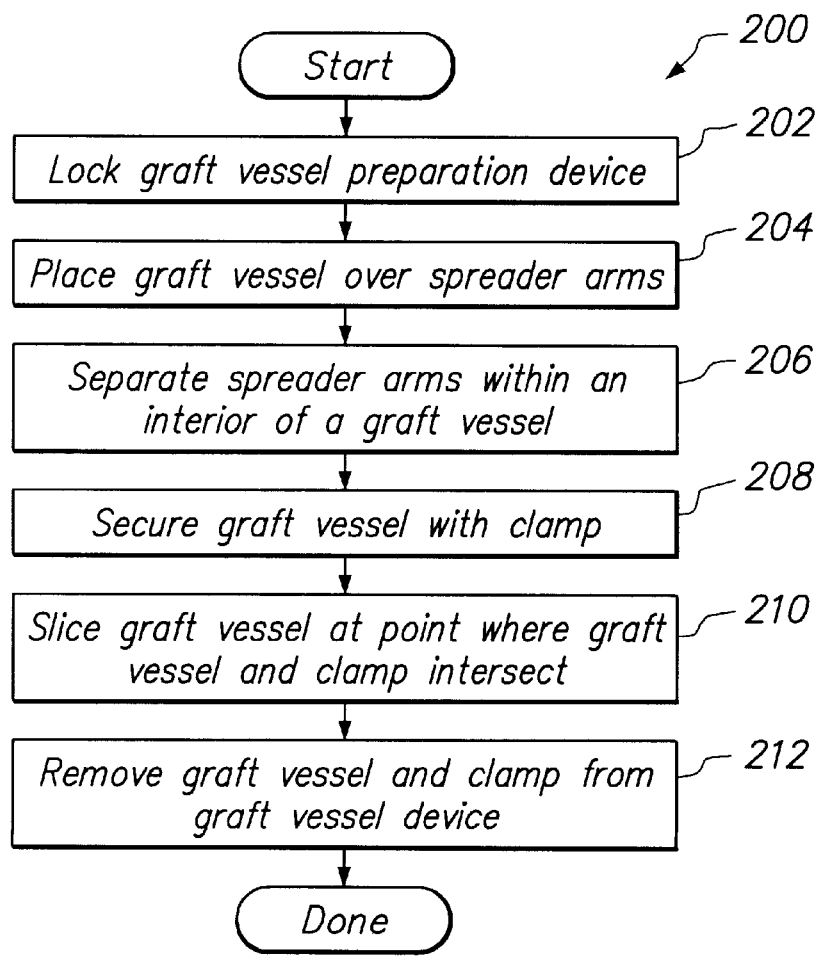
FIG. 8 illustrates a method for slicing a graft vessel in preparation for a grafting procedure in accordance with one embodiment of the present invention.

Now making reference to FIG. 8, FIG. 8 illustrates a method 200 for slicing a graft vessel in preparation for a vascular anastomosis procedure, in accordance with one embodiment of the present invention. In operation 202 of the method 200, a graft vessel preparation device is locked. When the graft vessel preparation device is locked, spreader arms located on the graft vessel preparation device are adjacent to one another such that a single unit is formed. For example, the graft vessel preparation device 100 shown with respect to FIG. 1 is placed in a locked position such that the spreader arms 108a and 108b are adjacent to one another to form a single unit. Referring to FIG. 1, the clamp 103 clamps down onto the second base plate 102b to lock the graft vessel preparation device 100. When the clamp 103 clamps the second base plate 102b, the spreader arms 108a and 108b are held adjacent to each other to form a single unit. After the graft vessel preparation device 100 is placed in the locked position, an operation 204 is performed.

In the operation 204, a graft vessel is placed over the spreader arms of the graft vessel preparation device. The graft vessel is placed over the spreader arms such that the spreader arms occupy an interior of the graft vessel. Referring back to the example and FIG. 1, the graft vessel 112 is placed over the spreader arms 108a and 108b after the graft vessel preparation device 100 is locked. The graft vessel 112 is placed over the spreader arms 108a and 108b such that the spreader arms 108a and 108b occupy an interior of the graft vessel 112, as shown with respect to FIG. 1. Once the graft vessel 112 is placed over the spreader arms 108a and 108b, an operation 206 is performed.

In the operation 206, the spreader arms separate within an interior of the graft vessel. The spreader arms separate within the interior of the graft vessel until the spreader arms stretch the graft vessel. In one embodiment of the present invention, the graft vessel is stretched until a distance between the spreader arms is half the circumference of the graft vessel, such that the graft vessel is stretched flat. As the spreaders arms come into contact with the interior surface of the graft vessel, the spreader arms exert a force on the graft vessel which is equivalent to or less than the force exerted by the blood pressure of blood that normally flows through the graft vessel. Once the spreader arms separate within the graft vessel, the spreader arms may be pushed further into the graft vessel to fully support the end of the graft vessel. In addition, after the spreader arms separate within the graft vessel, the spreader arms may be locked to maintain the proper stretched configuration. Turning back to the example and FIG. 2, the spreader arms 108a and 108b separate within the interior of the graft vessel 112. As described earlier, the spreader arms 108a and 108b separate due to the force applied by the tension spring 114. The tension spring 114 continues to separate the spreader arms 108a and 108b within the graft vessel 112 until the spreader arms 108a and 108b are in contact with interior walls of the graft vessel 112. Once the spreader arms 108a and 108b fully separate within the interior of the graft vessel 112 and apply the desired force, the method performs an operation 208.

In operation 208, the graft vessel is secured with a clamp. When the clamp is secured to the graft vessel, incision points on the graft vessel are defined where the graft vessel and the clamp intersect with one another. The incision points define a critical dimension of the graft vessel and where the graft vessel will be sliced, as will be discussed further with reference to operation 210. Turning back to the example and FIG. 4A, the graft vessel preparation device 100 includes the first clamp portion 110a as previously described. Thus, as the graft vessel 112 was placed over the spreader arms 108a and 108b in the operation 204, the graft vessel 112 was laid over the first clamp portion 110a. Therefore, in the operation 208, the second clamp portion 110b is attached to the first clamp portion 110a (shown with reference to FIG. 1) with the fasteners 116 to form the clamp 110. The intersection of the clamp 110 and the graft vessel 112 define the incision points 120a and 120b where the graft vessel is to be sliced in the operation 210.

Prior to slicing the graft vessel in the operation 210, the spreader arms are mounted further within the interior of the graft vessel. The spreader arms are pushed further within the graft vessel in order to assist the incisors in the slicing operation. In this embodiment, the spreader arms contain grooves which provide a surface for the incisors as the incisors slice graft vessel. Moreover, the groove provides a track which facilitates the slicing of the graft vessel during the slicing operation described with respect to the operation 210.

In the operation 210, the graft vessel is sliced after the graft vessel is secured with the clamp in the operation 208. Referring back to FIG. 4A and the example, the incisors 118a and 118b slice the graft vessel 112 from the incision points 120a and 120b outward to an end of the graft vessel 112. As described earlier, the incision made in the graft vessel 112 is made such that the graft vessel 112 may be properly grafted to the target vessel 124 during the vascular anastomosis procedure. Once the graft vessel 112 is sliced in the operation 210, the graft vessel 112 and the clamp 110 are removed from the graft vessel preparation device 100 in operation 212. The graft vessel 112 and the clamp 110 are removed from the graft vessel preparation device 100 by disengaging the clamp 110 from the graft preparation device 100 and sliding the graft vessel 112 off of the spreader arms 108a and 108b. After the operation 212 is complete, the graft vessel 212 is ready for grafting to a target vessel during the vascular anastomosis procedure.

Figure 9:
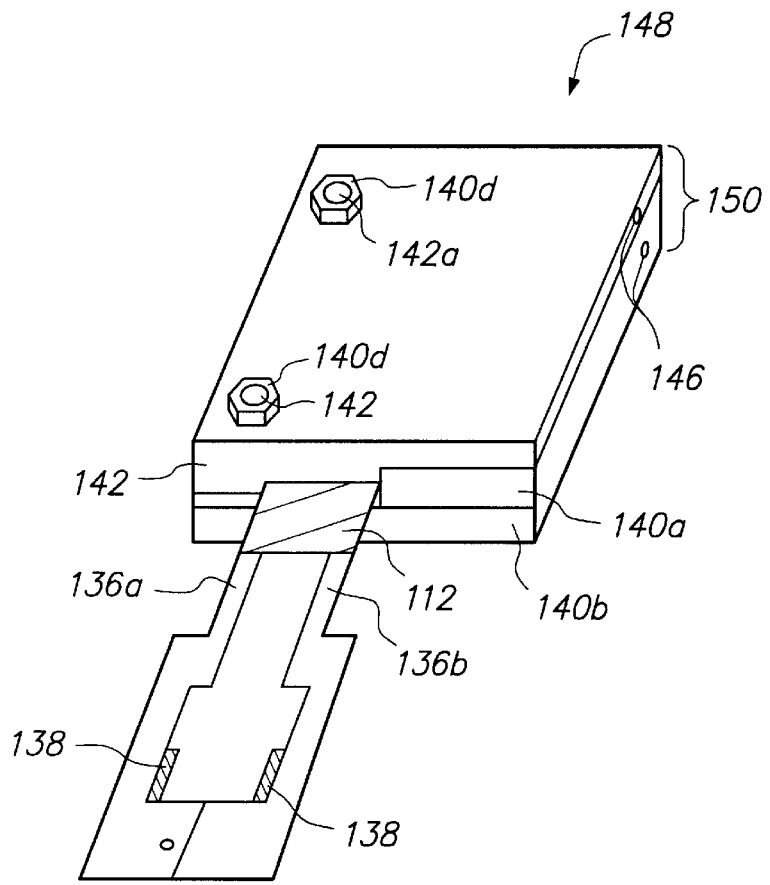
FIG. 9 illustrates a perspective view of graft vessel preparation device in accordance with an embodiment of the present invention.

Now making reference to FIG. 9, FIG. 9 illustrates a graft vessel preparation device or flapper 148 in accordance with an alternative embodiment of the present invention. In this embodiment, the graft vessel flapper includes a locator clamp 150 having alignment holes 146 and a spreader 136. The alignment holes 146 align the locator clamp 150 with the anastomosis tool 132. In addition, the alignment holes 146 facilitate proper engagement of the graft vessel flapper 148 with the anastomosis tool 132, as will be further discussed with reference to FIG. 16. The locator clamp 150 establishes the critical dimension Y (not shown) of the graft vessel 112, as will be further discussed with reference to FIGS. 12 through 14B. The spreader 136 includes a first spreader arm 136a and a second spreader arm 136b, as more clearly shown with reference to FIG. 10A.

Figure 10A:
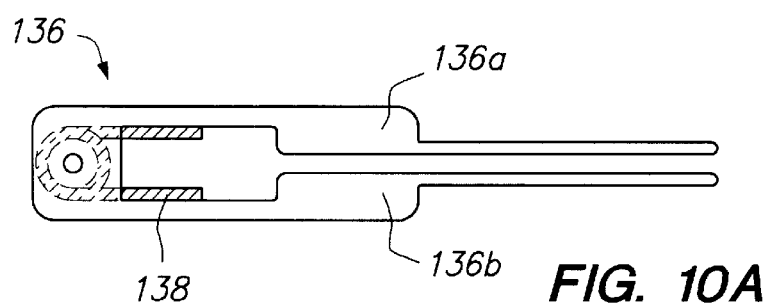
FIG. 10A shows a side view of a spreader of the graft vessel preparation device of FIG. 9, in accordance with one embodiment of the present invention.

FIG. 10A shows the spreader 136, in accordance with one embodiment of the present invention. The spreader 136 includes the first spreader arm 136a and the second spreader arm 136b which are movable with respect to one another. The spreader arms 136a and 136b are moved with respect to one another by a spring 138. The spring 138 is a torsion spring in one embodiment of the present invention which connects the first spreader arm 136a to the second spreader arm 136b. The spring 138 attaches to a distal end of the first spreader arm 136a and a distal end of the second spreader arm 136b. The spring 138 may be any suitable type of spring which separates the first spreader arm 136a from the second spreader arm 136b, such as a torsion spring, a leaf spring, a compression spring, an elastomer having spring-like characteristics, or the like. In one embodiment of the present invention. The spring 138 is a torsion spring having a spring rate in preferably in a range between about 0.001 lbs./deg. to about 0.01 lbs./deg. and more preferably about 0.00156 lbs./deg. The first spreader arm 136a and the second spreader arm 136b are configured to receive the graft vessel 112 when the spreader 136 is in a locked position, as shown with reference to FIG. 10B.

Figure 10B:
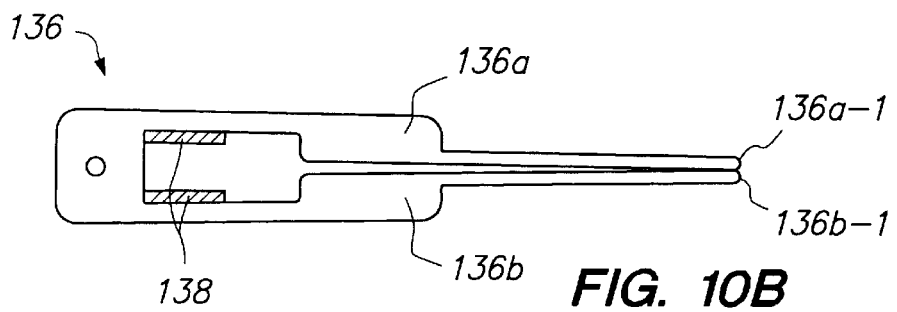
FIG. 10B illustrates a side view of the spreader of FIG. 10A, where the spreader is in a locked position in accordance with one embodiment of the present invention.

FIG. 10B illustrates the spreader 136 in a locked or closed position, in accordance with another embodiment of the present invention. The spreader 136 is locked when an end 136a-1 of the first spreader arm 136a makes contact or is positioned substantially adjacent to an end 136b-1 of the second spreader arm 136b, as shown with reference to FIG. 10B. The spreader 136 is placed into the locked position using any suitable technique, such as a clip, a clamp or the like. When the spreader arms 136a and 136b are placed in the locked position, the spreader 136 receives the graft vessel 112, as shown with reference to FIG. 11.

Figure 11:
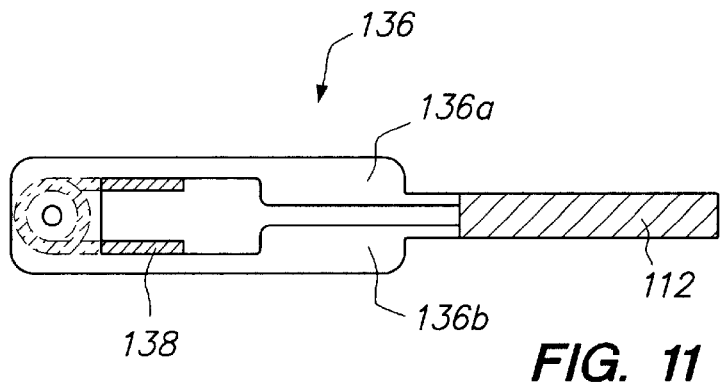
FIG. 11 shows a side view of the spreader of FIG. 10A, where graft vessel placed over the spreader in accordance with another embodiment of the present invention.
Figure 12:
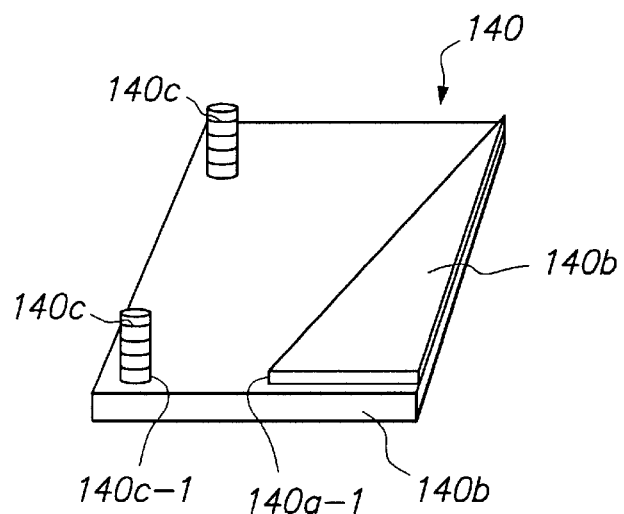
FIG. 12 shows a perspective view of a critical dimension locator of the graft vessel preparation device of FIG. 9, in accordance with one embodiment of the present invention.

FIG. 11 shows the graft vessel 112 placed over the spreader 136, in accordance with one embodiment of the present invention. Once the graft vessel 112 is placed over the spreader 136, the first spreader arm 136a and the second spreader arm 136b separate within an interior of the graft vessel 112. The spreader arms 136a and 136b separate by the action of the spring 138. The first spreader arm 136a and the second spreader arm 136b separate until the first spreader arm 136a and the second spreader arm 136b are adjacent interior walls of the graft vessel 112 and stretch the graft vessel 112 a desired amount which simulates the condition of the graft vessel when implanted in the body.

Turning back to the graft vessel flapper 148 shown with respect to FIG. 9, the graft vessel flapper also includes the locator clamp 150. The locator clamp 150 includes a critical dimension locator 140, as more clearly shown with reference to FIG. 12. The critical dimension locator 140 has a raised portion 140a, a base 140b and threaded fasteners 140c. The raised portion 140a is rigidly attached to the base 140b and may be formed into the base 140b using any suitable techniques, such as spot welding, injection molding, or the like. In the embodiment shown with respect to FIG. 12, the raised portion 140a is in a triangular configuration. However, it should be noted that the raised portion 140a may have any orientation which allows for the establishment of a critical dimension Y for the graft vessel 112, as will be more fully discussed with reference to FIG. 13A. It should also be noted that in an alternative embodiment of the present invention, the raised portion 140a is not rigidly attached to the critical dimension locator 140. Thus, as will be more fully discussed with reference to FIG. 13A, once a graft vessel is placed on the critical dimension locator 140, the raised portion 140a may also be coupled with the critical dimension locator 140. The threaded fastener 140c allows connection between the critical dimension locator 140 and a second clamp half 142 (not shown). The threaded fastener 140c may be any type of fastener suitable for connecting the critical dimension locator 140 with the second clamp half 142. Also, the threaded fastener 140c has an edge 140c-1 and the raised portion 140a includes an edge 140a-1. The raised portion 140a, along with the threaded fastener 140c, establishes a critical dimension Y for the graft vessel 112 defined between the edges 140a-1 and 140c-1, as shown with reference to FIGS. 13A and 13B.

Figure 13A:
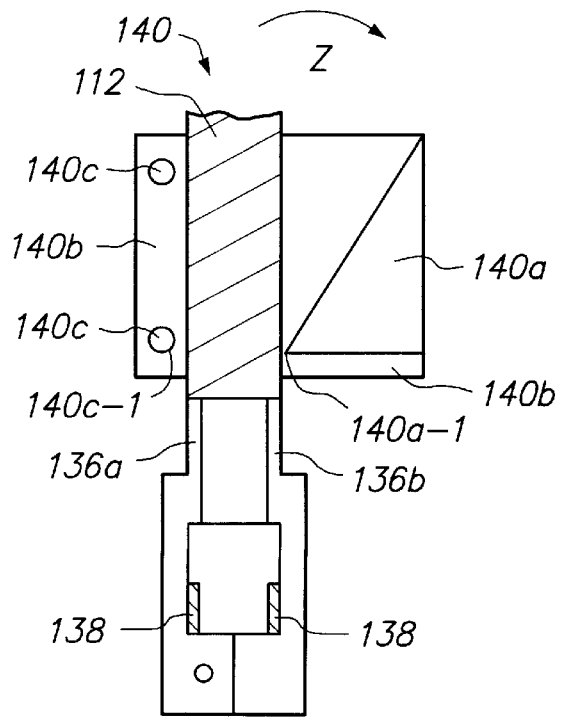
FIG. 13A is an embodiment of the present invention where the spreader and graft vessel of FIG. 10B are engaged with the critical dimension locator of FIG. 12.

FIG. 13A is an embodiment of the present invention showing the spreader 136, along with the graft 112, engaged with the critical dimension locator 140. After the first spreader arm 136a and the second spreader arm 136b separate within the interior of the graft vessel 112, the spreader 136, along with the graft vessel 112, is placed on to the critical dimension locator 140 in order to establish the critical dimension Y. Initially, the spreader 136 and the graft vessel 112 are placed in the critical dimension locator 140 such that the graft vessel 112 resides between the edges 140a-1 and 140c-1. After the spreader 136 and the graft vessel 112 are placed within the critical dimension locator 140, the spreader 136 and the graft vessel 112 are rotated in a clockwise direction Z on the critical dimension locator 140, as shown with respect to FIG. 13B.

Figure 13B:
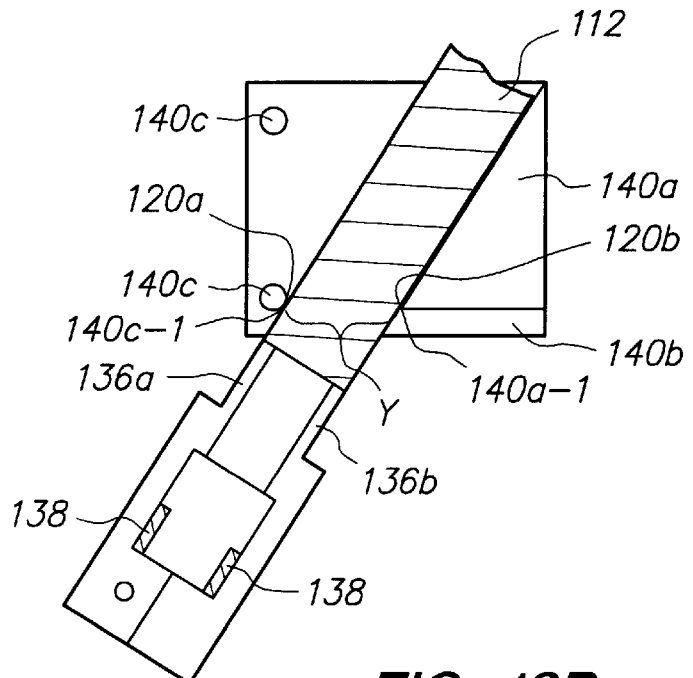
FIG. 13B shows the spreader and the graft vessel of FIG. 13A rotated clockwise within the critical dimension locator of FIG. 13A in order to establish a critical dimension Y in accordance with one embodiment of the present invention.

FIG. 13B shows the spreader 136, along with the graft vessel 112, rotated clockwise within the critical dimension locator 140 in order to establish the critical dimension Y, in accordance with one embodiment of the present invention. The spreader 136 and the graft vessel 112 are rotated until the graft vessel 112 comes into contact with the edges 140a-1 and 140c-1 at contact points 120a and 120b, as shown with reference to FIG. 13B. As previously described, the contact points 120a and 120b are the endpoints for the critical dimension Y. In addition, as previously discussed, the critical dimension Y allows for proper grafting of the graft vessel to a target vessel during a vascular anastomosis procedure. Once the critical dimension Y is established on the graft vessel 112, the second clamp half 142 is attached to the critical dimension locator 140.

Figure 14A:
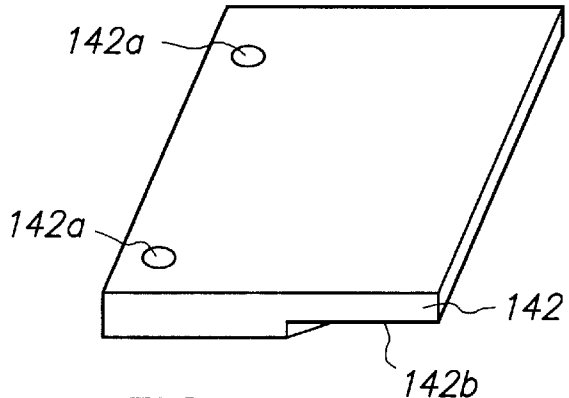
FIG. 14A shows a perspective view of a second clamp half of the graft vessel preparation device of FIG. 9, in accordance with one embodiment of the present invention.

The second clamp half 142 is more clearly shown with reference to FIG. 14A. The second half clamp 142 includes through holes 142a and a recess 142b. The through holes 142a allow for passage of the threaded fasteners 140c of the critical dimension locator 140 through the second half clamp 142 such that the second clamp half 142 may attach to the critical dimension locator 140. The recess 142b allows the raised portion 140a to fit within the second half clamp 142 when the second clamp half 142 is attached to the critical dimension locator 140, as shown with reference to FIG. 9.

Figure 14B:
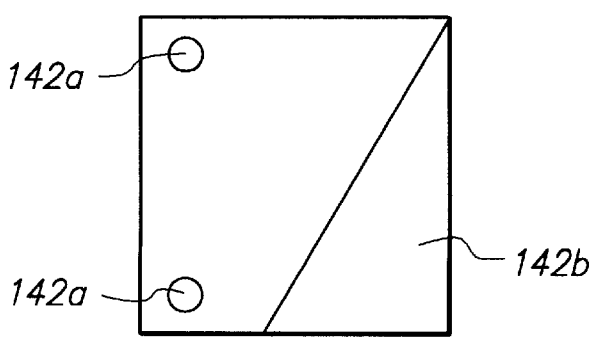
FIG. 14B shows a bottom view of the second clamp half of FIG. 14A, in accordance with one embodiment of the present invention.

In this embodiment of the present invention, the recess 142b has a triangular configuration as shown with respect to FIG. 14B such that the critical dimension locator 140 will fit flush with the second half clamp 142. It should be noted that the configuration of the recess 142b complements the configuration of the raised portion 140a. Thus, if in an alternative embodiment of the present invention, the raised portion 140a contains a square configuration, the recess 142b will also have a square configuration.

Returning to FIG. 9 and the graft vessel flapper 148, once the critical dimension Y is established on the graft vessel 112, the second clamp half 142 is securely attached to the critical dimension locator 140 to form the locator clamp 150. The second clamp half 142 is securely attached to the critical dimension locator 140 by passing the threaded fasteners 140a through the through holes 142a of the second clamp half 142. A fastener 140d is then fixed to the threaded fasteners 140c. In one embodiment of the present invention, the fastener 140d may be any suitable type of fastener which securely attaches the second clamp half 142 to the critical dimension locator 140, such as a threaded nut or the like. Once the locator clamp 150 traps and secures the graft vessel 112 in place, the graft vessel 112 is sliced, as shown with reference to FIG. 15.

Figure 15:
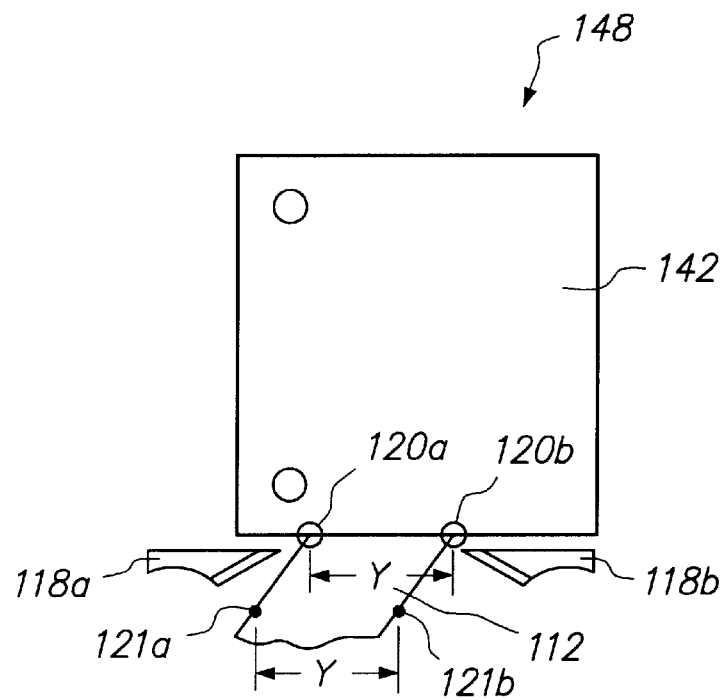
FIG. 15 shows a top view of the slicing of the graft vessel of FIG. 13B with incisors in accordance with one embodiment of the present invention.

FIG. 15 shows the graft vessel 112 being sliced with the incisors 118a and 118b, in accordance with one embodiment of the present invention. The incisors 118a and 118b slice the graft vessel 112 from the incision points 120a and 120b outward to an end of the graft vessel 112 in order to maintain the critical dimension Y. It should also be noted that in an alternative embodiment of the present invention, the incisors 118a and 118b may slice the graft vessel 112 at any point, as long as the critical dimension Y is maintained. For example, the incisors 118a and 118b may slice the graft vessel 112 at the points 121a and 121b, which, as may be seen with reference to FIG. 15, maintain the critical dimension Y. As described earlier, the incisors 118a and 118b may be any type of cutting device suitable for slicing graft vessels, such as a scalpel, a pair of scissors or the like. Once the graft vessel 112 is sliced, the graft vessel flapper 148 is attached to the anastomosis tool 132 in preparation for grafting during the vascular anastomosis procedure, as shown with reference to FIG. 16.

Figure 16:
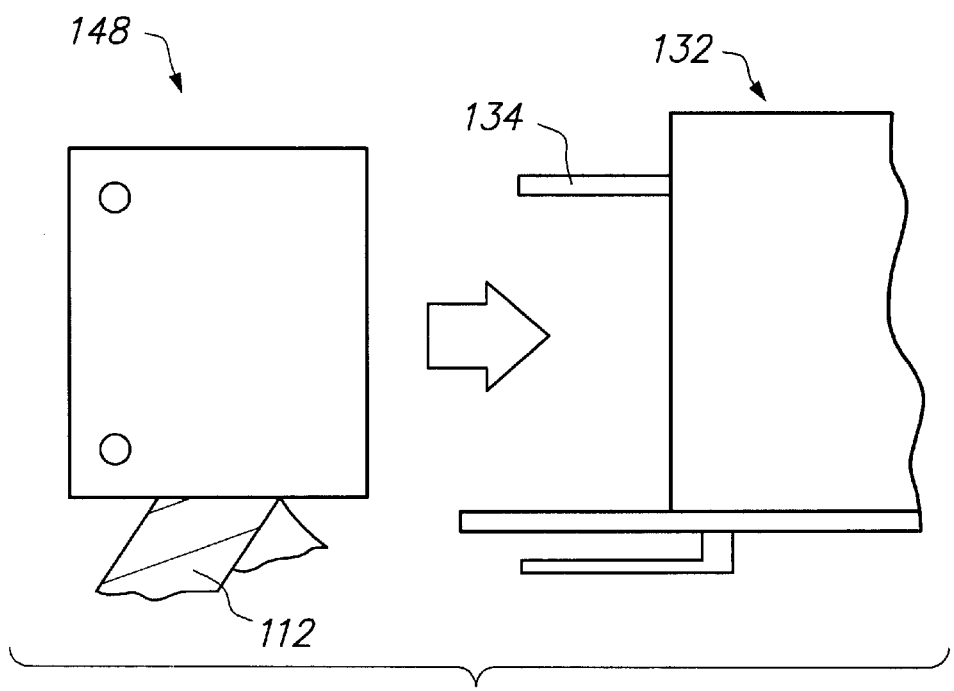
FIG. 16 illustrates the insertion of the graft vessel preparation device of FIG. 9 onto a anastomosis tool in accordance with one embodiment of the present invention.

FIG. 16 illustrates the insertion of the graft vessel flapper 148 onto the anastomosis tool 132, in accordance with one embodiment of the present invention. As previously mentioned, the anastomosis tool 132 grafts the graft vessel 112 to the target vessel 124 during the vascular anastomosis procedure. The vascular anastomosis procedure is performed using the anastomosis tool 132. Thus, the graft vessel flapper 148 and the graft vessel 112 must be attached to the anastomosis tool 132 in order to complete the vascular anastomosis procedure. The graft vessel flapper 148 is attached to the anastomosis tool 132 via the alignment holes 146. The alignment holes 146 fit over the alignment pins 134 in order to ensure proper fitment of the graft vessel flapper 148 with the anastomosis tool 132. As described earlier, proper fitting of the graft vessel flapper 148 with the anastomosis tool 132 is necessary for proper grafting of the graft vessel 112 to the target vessel 124 during the vascular anastomosis procedure. Once the graft vessel flapper 148 and the graft vessel 112 are attached to the anastomosis tool 132, the vascular anastomosis procedure is performed.

Figure 17:
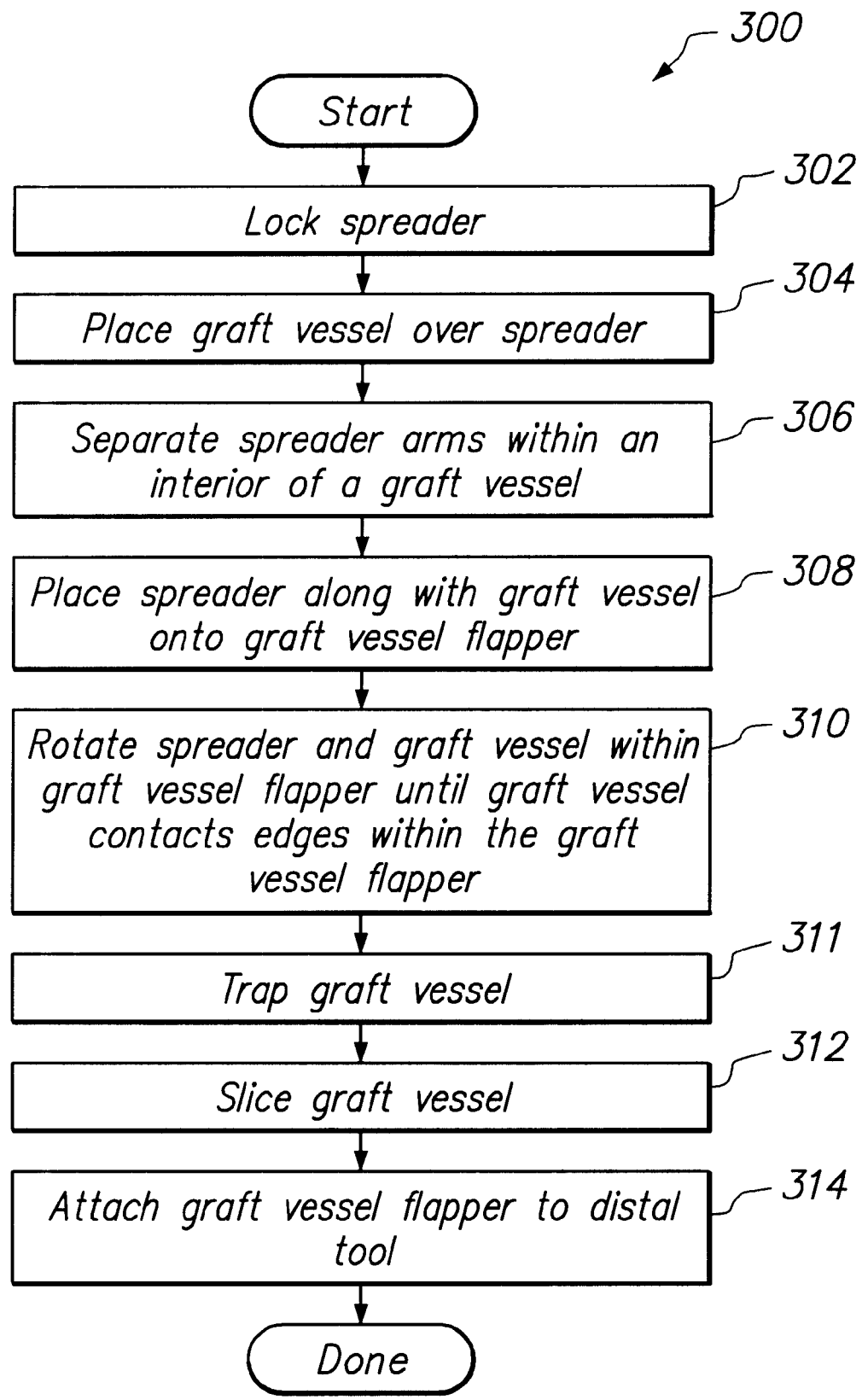
FIG. 17 shows a method for preparing a graft vessel for an anastomosis procedure in accordance with one embodiment of the present invention.

Now making reference to FIG. 17 and a method 300, FIG. 17 shows the method 300 for preparing a graft vessel for an anastomosis procedure in accordance with one embodiment of the present invention. In the method 300, an operation 302 is first performed where a spreader is locked. The spreader is locked in order to allow the placement of a graft vessel over the spreader. For example, turning to FIG. 10B, the spreader 136 is placed in a locked position. As described earlier, the spreader 136 may be locked using any suitable technique, including a clamp, a clip, or simply pinching closed the spreader with a user's fingers such that spreader arms of the spreader are held together. As may be seen with respect to FIG. 10B, the spreader 136 is locked such that the first spreader arm 136a contacts the second spreader arm 136b at the ends 136a-1 and 136b-1. When the spreader 136 is placed in the locked position, the spreader 136 is configured to receive a graft vessel, as described with respect to an operation 304.

The operation 304 in FIG. 17 is performed once the spreader is locked. In the operation 304, a graft vessel is placed over the spreader while the spreader is in the locked position. After the graft vessel is placed over the spreader in the operation 304, the spreader arms of the spreader are separated within an interior of the graft vessel in the operation 306. Turning back to the example and FIG. 11, once the graft vessel 112 is placed over the spreader 136 in the operation 304, the first spreader arm 136a and the second spreader arm 136b separate from each other within the interior of the graft vessel 112. The spring 138 separates the first spreader arm 136a from the second spreader arm 136b. The first spreader arm 136a and the second spreader arm 136b continue to separate from one another until both the spreader arms 136a and 136b come into contact with an interior surface of the graft vessel 112. Once the first spreader arm 136a and the second spreader arm 136b separate within the graft vessel 112 in the operation 306, an operation 308 is performed.

In the operation 308, the spreader, along with the graft vessel, is placed onto a graft vessel flapper. As described earlier with reference to the graft vessel flapper 148, the graft vessel flapper establishes a critical dimension on the graft vessel. Turning back to the example and FIG. 13A, the critical dimension locator 140 forms part of the graft vessel flapper 148. As such, the spreader 136 and the graft vessel 112 are placed in the critical dimension locator 140. After the spreader 136 is placed in the critical dimension locator 140, an operation 310 is performed.

In the operation 310, the spreader and the graft vessel are rotated within the graft vessel flapper. The spreader is rotated until the graft vessel comes into contact with edges of the graft vessel flapper. The edges of the graft vessel flapper establish the endpoints of the critical dimension when the graft vessel contacts the edges, thereby establishing the critical dimension on the graft vessel. Referring back to the example and FIG. 13A, the spreader 136 and the graft vessel 112 are rotated in the clockwise direction Z until the graft vessel 112 comes into contact with the edges 140a-1 and 140c-1 of the critical dimension locator 140, as shown with reference to FIG. 13B. The graft vessel 112 contacts the edges 140a-1 and 140c-1 at the endpoints 120a and 120b. As previously described, the endpoints 120a and 120b establish the critical dimension Y. Once the critical dimension Y is established in the operation 310, the graft vessel 112 is trapped in operation 311.

The graft vessel 112 is trapped in the operation 311 as a second clamp half is attached to graft vessel flapper. When the second half clamp is attached to the graft vessel flapper, the graft vessel flapper holds the critical dimension Y. Turning back to the example and FIG. 15, the second clamp half 142 is attached to the graft vessel flapper 148. When the second clamp half 142 is attached to the graft vessel flapper 148 when the threaded fasteners 140c pass through the through holes 142a and secured with the fasteners 140d. Once the graft vessel 112 is trapped in the graft vessel flapper 148, the graft vessel 112 is sliced in an operation 312.

Once the graft vessel is sliced in the operation 312, the graft vessel flapper is attached to a anastomosis tool in the operation 314. As described earlier, the anastomosis tool facilitates grafting of the graft vessel to a target vessel during a vascular anastomosis procedure. Making reference to the example and FIG. 16, the graft vessel 112 is first sliced in the operation 312 and then attached to the anastomosis tool 132. As discussed earlier, the graft vessel flapper 148 attaches to the anastomosis tool 132 via the alignment holes 146 and alignment pins 134. Once the graft vessel flapper 148 and the graft vessel 112 are attached to the anastomosis tool 132, the graft vessel 112 is grafted to the target vessel 124 during the vascular anastomosis procedure. This grafting may be performed by any method suitable for grafting a graft vessel to a target vessel, such as suturing, stapling, tissue welding, clamping or the like.

The present invention now offers surgeons an automated method for accurately grafting a graft vessel to a target vessel. The prior art problems of dealing with the innate flexing tendencies of the graft vessel due to the small size and the flexible, circular configuration of the of the graft vessel are obviated with the present invention. Moreover, the graft vessel preparation device accurately and precisely allows the graft vessel to be a cut in a manner which allows a perimeter of the graft vessel end to be matched to a perimeter of an anastomosis site on a target vessel. Thus, the surgeon saves the time required to accurately and precisely slice the graft vessel, thereby decreasing the overall time a patient spends in surgery and decreasing the overall costs associated with spending time in surgery.

Furthermore, as discussed earlier, when a surgeon grafts a graft vessel to a target vessel, an assistant may be required to hold the edges of the graft vessel and assist in preparing the graft vessel for the anastomosis procedure. The clamp of the present invention holds the graft vessel as the graft vessel is placed in the anastomosis tool. The clamp of the present invention also holds the graft vessel during the anastomosis procedure. As such, the need for an assistant to hold the graft vessel during grafting is avoided with the present invention, thereby further reducing the time and the overall costs associated with performing a grafting procedure on a patient.

The above are exemplary modes of carrying out the invention and are not intended to be limiting. It will be apparent to those of ordinary skill in the art that modifications thereto can be made without departure from the spirit and scope of the invention as set forth in the following claims.

What is claimed is:

1. A graft vessel preparation device for preparing a graft vessel for a vascular anastomosis procedure, the preparation device comprising:
    a spreader configured to receive and stretch an end portion of the graft vessel;
    a critical dimension locator configured to establish a critical dimension on the graft vessel when the graft vessel is received on the spreader; and
    a clamp configured to coordinate with both the spreader and the critical dimension locator in order to fix the critical dimension on the graft vessel.

2. A graft vessel preparation device as recited in claim 1, the graft vessel preparation device further comprising:
    two base plates rigidly attached to the spreader.

3. A graft vessel preparation device as recited in claim 2, the graft vessel preparation device further comprising:
    an extension link rotatably attached to the two base plates.

4. A graft vessel preparation device as recited in claim 3, wherein the clamp rotatably attaches to the two base plates.

5. A graft vessel preparation device as recited in claim 4, the graft vessel preparation device further comprising:
    a spring attached to one of the two base plates and fixed to a second surface, whereby a tensile force of the spring places tension on the graft vessel preparation device in order to rotate the extension link.

6. A graft vessel preparation device as recited in claim 5, wherein the extension link rotates a given angle.

7. A graft vessel preparation device as recited in claim 6, wherein the clamp rotates the given angle.

8. A graft vessel preparation device as recited in claim 1, wherein the critical dimension corresponds to a length of an anastomosis and allows proper grafting of the graft vessel to a coronary vessel during a vascular anastomosis procedure.

9. A graft vessel preparation device as recited in claim 1, wherein the spreader further comprises:
    a first spreader arm having a first end;
    a second spreader arm having a first end; and
    a spring attached to both the first end of the first spreader arm and the first end of the second spreader arm such that the first spreader arm is biased apart from the second spreader arm to stretch an end portion of the graft vessel.

10. A graft vessel preparation device as recited in claim 9, wherein the first spreader arm and the second spreader arm have second ends configured to receive the end portion of the graft vessel.

11. A graft vessel preparation device as recited in claim 1, wherein the clamp further comprises:
    a first half; and
    a second half that attaches to the first half, where the first half and the second half are configured to receive both the graft vessel and the spreader.

12. A graft vessel preparation device as recited in claim 11, wherein the first half of the clamp forms the critical dimension locator.

13. A graft vessel preparation device as recited in claim 12, wherein the critical dimension locator further includes:
    a first edge; and
    a second edge, where the first edge and the second edge are configured to receive the graft vessel in order to establish the critical dimension on the graft vessel.

14. A graft vessel preparation device as recited in claim 1, wherein the clamp captures the critical dimension established by the critical dimension locator.

15. A graft vessel preparation device as recited in claim 14, wherein the clamp provides for the transfer of the graft vessel to a target vessel while maintaining the critical dimension.

16. A graft vessel preparation device for preparing a graft vessel for a vascular anastomosis procedure, the preparation device comprising:
    a parallelogram linkage;
    a first spreader arm and a second spreader arm mounted substantially parallel to one another on opposing members of the parallelogram linkage, the spreader arms being movable with respect to one another by motion of the parallelogram linkage, the spreader arms being configured to receive an end of the graft vessel over the spreader arms and to move apart by action of the parallelogram linkage to establish a critical dimension on the graft vessel.

17. A graft vessel preparation device as recited in claim 16, the preparation device further including:
    a clamp configured to hold the graft vessel and maintain the critical dimension.

18. A graft vessel preparation device as recited in claim 16, the preparation device further comprising:
    two base plates attached to the parallelogram linkage, wherein the spreader arms are attached to the two base plates.

19. A graft vessel preparation device as recited in claim 18, wherein expansion links connect the two base plates.

20. A graft vessel preparation device as recited in claim 19, wherein the expansion links rotate to move the spreader arms apart to establish the critical dimension.

21. A graft vessel preparation device as recited in claim 20, the preparation device further comprising:
    a spring attached to one of the base plates and fixed to a second surface, whereby a tensile force of the spring rotates the expansion links.

22. A graft vessel preparation device as recited in claim 21, wherein the critical dimension corresponds to a length of an anastomosis and allows proper grafting of the graft vessel to a target vessel during the vascular anastomosis procedure.

23. A graft vessel preparation device for preparing a graft vessel for a vascular anastomosis procedure, the preparation device comprising:
   a base having a first part and a second part movable with respect to each other;
   a first spreader arm attached to the first part of the base and a second spreader arm attached to the second part of the base, the spreader arms configured to receive an end of the graft vessel over themselves;
   an extension link rotatably attached to the base, the extension link being configured to separate the spreader arms; and
   a holding clamp for clamping the graft vessel, where the holding clamp is substantially aligned with the extension link.

24. A graft vessel preparation device as recited in claim 23, the graft vessel preparation device further comprising:
   a spring attached to the graft vessel preparation device wherein the spring places a tension on the graft vessel preparation device in order to rotate the extension link.

25. A graft vessel preparation device as recited in claim 23, wherein the holding clamp further comprises:
   a first clamp portion rotatably attached to the base; and
   a second clamp portion which attaches to the first clamp portion and traps the graft vessel.

26. A graft vessel preparation device as recited in claim 25, wherein the first clamp portion is configured to rotate a given angle when the extension link rotates the given angle.

27. A graft vessel preparation device as recited in claim 23, wherein the holding clamp further comprises:
   aligning features to facilitate alignment of the holding clamp with a anastomosis tool, the anastomosis tool being configured to perform the vascular anastomosis procedure.

28. A graft vessel preparation device as recited in claim 23, wherein the holding clamp is rigidly attached to the base.

29. A method for preparing a graft vessel for an anastomosis procedure using a graft vessel preparation device, the graft vessel preparation device including spreader arms movable with respect to each other, the method comprising:
   placing the graft vessel over the spreader arms such that the spreader arms occupy an interior of the graft vessel;
   moving the spreader arms away from one another to stretch the graft vessel; and
   establishing a critical dimension on the stretched graft vessel.

30. A method for preparing a graft vessel as recited in claim 29, the method further comprising:
   slicing the stretched graft vessel.

31. A method for preparing a graft vessel as recited in claim 30, further comprising:
   biasing the spreader arms apart from one another, wherein the moving results from the biasing.

32. A method for preparing a graft vessel as recited in claim 31, wherein the spreader arms are separated using a parallelogram linkage which includes an expansion link attached to a base of the graft vessel preparation device.

33. A method for preparing a graft vessel as recited in claim 32, the method further comprising:
   rotating the expansion link with a spring, where a tensile force of the spring rotates the expansion link.

34. A method for preparing a graft vessel as recited in claim 33, where the operation of establishing the critical dimension further includes:
   clamping the stretched graft vessel with a clamp.

35. A method for preparing a graft vessel as recited in claim 34, wherein the clamp includes a first clamp portion and a second clamp portion, the first clamp portion being rotatably attached to the graft vessel preparation device and the second clamp portion attaching to the first clamp portion with mounting screws.

36. A method for preparing a graft vessel as recited in claim 35, the method further comprising:
   mounting the second clamp portion to the first clamp portion after the spreader arms are separated within the interior of the stretched graft vessel.

37. A method for preparing a graft vessel as recited in claim 36, wherein the critical dimension is established along one edge of the clamp.

38. A method for preparing a graft vessel as recited in claim 37, wherein the critical dimension of the stretched graft vessel allows for proper grafting of the stretched graft vessel to a target vessel.

39. A method for preparing a graft vessel as recited in claim 38, wherein the clamp includes alignment holes.

40. A method for preparing a graft vessel as recited in claim 39, the method further comprising:
   extracting the stretched graft vessel from the graft vessel preparation device wherein the clamp holds the critical dimension of the stretched graft vessel during the extraction operation.

41. A method for preparing a graft vessel as recited in claim 40, the method further comprising:
   mounting the clamp onto a fastening device having alignment pins, where the alignment holes of the clamp fit over the alignment pins of the fastening device, thereby ensuring proper placement of the stretched graft vessel with the target vessel.

42. A method for preparing a graft vessel as recited in claim 41, wherein the fastening device is a anastomosis tool used for the anastomosis procedure.

43. A method for preparing a graft vessel as recited in claim 29, wherein the stretched graft vessel is placed over the spreader arms when the spreader arms are adjacent to each other such that the spreader arms form a single unit.

44. A preparation device for use with a graft vessel, comprising:
   spreader arms movable with respect to each other, wherein the spreader arms are adapted to receive the graft vessel; and
   a clamp rotatable with respect to the spreader arms, wherein the clamp is adapted to clamp the graft vessel received over the spreader arms and establish a critical dimension of the graft vessel.

45. A graft vessel preparation device as recited in claim 44, wherein the spreader arms have a locked position for placing the graft vessel over the spreader arms.

46. A graft vessel preparation device as recited in claim 45, wherein the spreader arms form a single unit when the spreader arms are in the locked position.

47. A graft vessel preparation device as recited in claim 46, the graft vessel preparation device further comprising:
   an extension link rotatably attached to the graft vessel preparation device, the extension link moving the spreader arms from the locked position to an expanded position for establishing the critical dimension.

48. A graft vessel preparation device as recited in claim 47, wherein the clamp further comprises:

a first clamp portion rotatably mounted to the graft vessel preparation device; and a second clamp portion which connects to the first clamp portion with mounting screws.

49. A graft vessel preparation device as recited in claim 48, wherein the clamp is substantially aligned with the extension link.

50. A graft vessel preparation device as recited in claim 44, wherein the spreader arms have a locked position after the spreader arms separate within the graft vessel.

51. A method for preparing a graft vessel using a graft vessel preparation device, the method comprising:

forming an incision in a target vessel having an incision perimeter; and preparing the graft vessel by establishing and maintaining a critical dimension of the graft vessel such that the incision perimeter of the target vessel is substantially the same as a perimeter of the critical dimension of the graft vessel.

52. A method for grafting a graft vessel as recited in claim 51, wherein the graft vessel preparation device includes a spreader having a first spreader arm and a second spreader arm movably attached to the first spreader arm with a torsion spring, where the first spreader arm and the second spreader arm are configured to receive an end of the graft vessel.

53. A method for grafting a graft vessel as recited in claim 52, wherein the graft vessel preparation device includes a critical dimension locator.

54. A method for grafting a graft vessel as recited in claim 53, wherein the critical dimension locator includes a first edge and a second edge opposite the first edge, where the first edge and the second edge are configured to define a critical dimension on the graft vessel.

55. A method for grafting a graft vessel as recited in claim 54, the method further comprising:

locking the spreader such that the first spreader arm and the second spreader arm are held together.

56. A method for grafting a graft vessel as recited in claim 55, the method further comprising:

placing the end of the graft vessel over the first spreader arm and the second spreader arm when the spreader is held together such that the first spreader arm and the second spreader arm occupy an interior of the graft vessel.

57. A method for grafting a graft vessel as recited in claim 56, the method further comprising:

separating the first spreader arm from the second spreader arm within the interior of the graft vessel.

58. A method for grafting a graft vessel as recited in claim 57, the method further comprising:

attaching the spreader along with the graft vessel to the clamp such that the graft vessel resides between the first edge and the second edge of the critical dimension locator.

59. A method for grafting a graft vessel as recited in claim 57, the method further comprising:

locking the first spreader arm and the second spreader arm after the first spreader arm and the second spreader arm separate within the interior of the graft vessel.

60. A method for grafting a graft vessel as recited in claim 58, the method further comprising:

rotating the spreader along with the graft vessel within the critical dimension locator such that the graft vessel contacts the first edge and the second edge in order to establish the critical dimension on the graft vessel.

61. A method for grafting a graft vessel as recited in claim 60, the method further comprising:

slicing the graft vessel such that the critical dimension is maintained on the graft vessel.

62. A method for grafting a graft vessel as recited in claim 61, wherein the clamp includes alignment holes which allow connection between the clamp and a anastomosis tool.

63. A method for grafting a graft vessel as recited in claim 62, the method further comprising:

attaching the clamp to the anastomosis tool with the alignment holes to perform a vascular anastomosis procedure.

64. A method for grafting a graft vessel as recited in claim 63, wherein the critical dimension corresponds to a length of an anastomosis and allows proper grafting of the graft vessel to a coronary vessel during the vascular anastomosis procedure.

* * * * *